United States Patent [19]

Hoffman

[11] Patent Number: 5,057,822
[45] Date of Patent: Oct. 15, 1991

[54] MEDICAL GAS ALARM SYSTEM

[75] Inventor: Richard E. Hoffman, Overland Park, Kans.

[73] Assignee: Puritan-Bennett Corporation, Lenexa, Kans.

[21] Appl. No.: 578,625

[22] Filed: Sep. 7, 1990

[51] Int. Cl.⁵ .............................................. G08B 21/00
[52] U.S. Cl. .................................... 340/611; 340/603; 340/606; 128/202.22; 128/205.23; 137/554; 137/557
[58] Field of Search ............... 340/611, 603, 606, 608, 340/626; 128/205.23, 202.22; 137/551, 552, 554, 557; 200/81 R; 73/861, 861.02

[56] References Cited

U.S. PATENT DOCUMENTS

| | | |
|---|---|---|
| 1,210,738 | 1/1917 | Ward . |
| 3,529,625 | 9/1970 | Ferrari . |
| 3,807,446 | 4/1974 | Driskell et al. . |
| 4,176,617 | 12/1979 | Pilipski . |
| 4,345,612 | 8/1982 | Koni et al. . |
| 4,573,115 | 2/1986 | Halgrimson . |
| 4,598,279 | 7/1986 | Nowacki et al. ........... 128/202.22 X |
| 4,667,669 | 5/1987 | Pasternack ................. 128/202.22 X |
| 4,879,547 | 11/1989 | Pryslak . |

FOREIGN PATENT DOCUMENTS

| | | | |
|---|---|---|---|
| 8905938 | 6/1989 | PCT Int'l Appl. ................ | 137/554 |
| 2141825 | 1/1985 | United Kingdom ............... | 340/611 |

Primary Examiner—Jin F. Ng
Assistant Examiner—Jeffery A. Hofsass
Attorney, Agent, or Firm—Hovey, Williams, Timmons & Collins

[57] ABSTRACT

A medical gas alarm system is provided which includes a sensor unit pneumatically connected to a medical gas supply line and a switch connected to a valve in the supply line for detecting the open condition of the valve. In the event either the sensor detects a high pressure or low pressure condition in the supply line or the switch is activated by closing of the valve, an alarm signal is received by an alarm module and an alarm is activated. The alarm may be visual, audible or both. During normal operations, the alarm module displays both a system on condition and a digital display indicating the pressure in the supply line. The invention also includes a method of monitoring the condition of a medical gas delivery system which includes sensing the pressure in the gas supply line, detecting the open condition of the valve, transmitting an alarm signal to an alarm module in response to alarm conditions detected either as a result of improper pressure or valve closure, and generating a humanly perceptible alarm warning in response to receipt of an alarm signal.

9 Claims, 2 Drawing Sheets

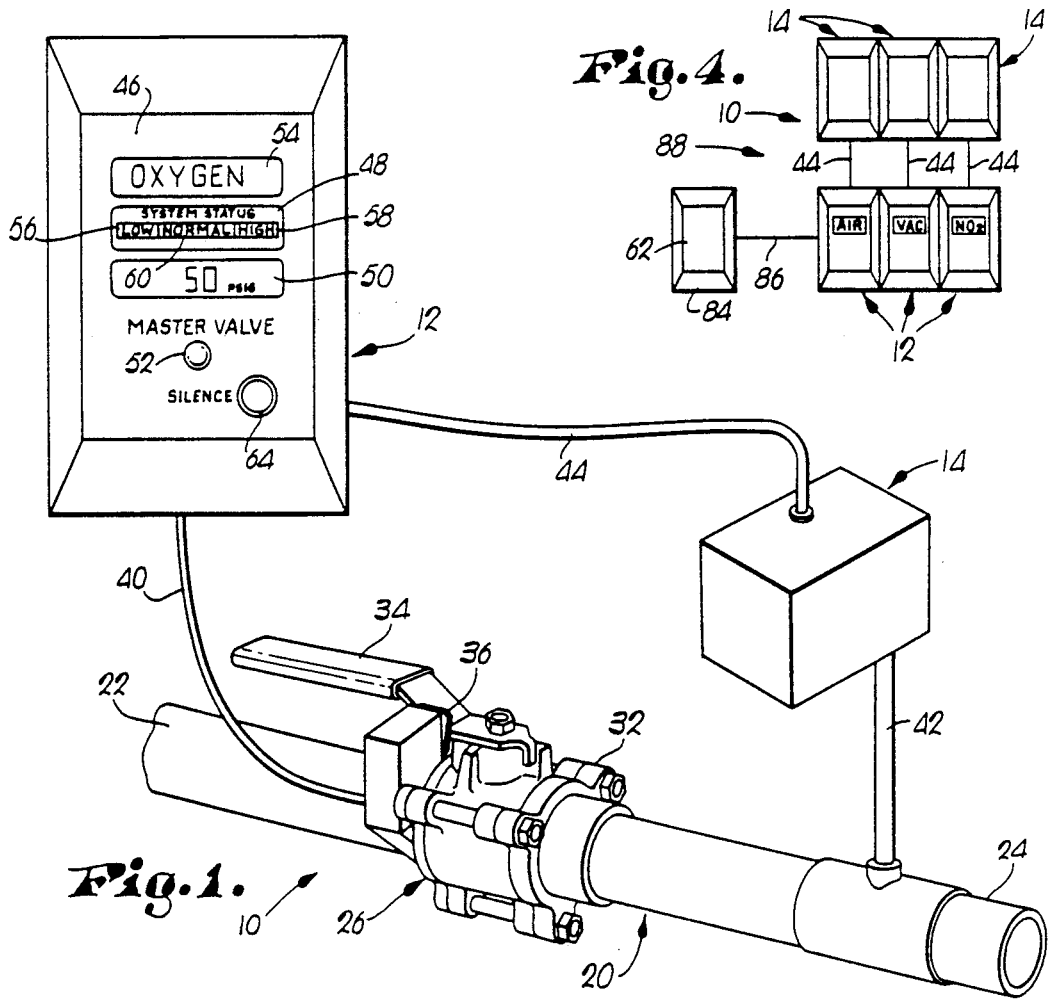
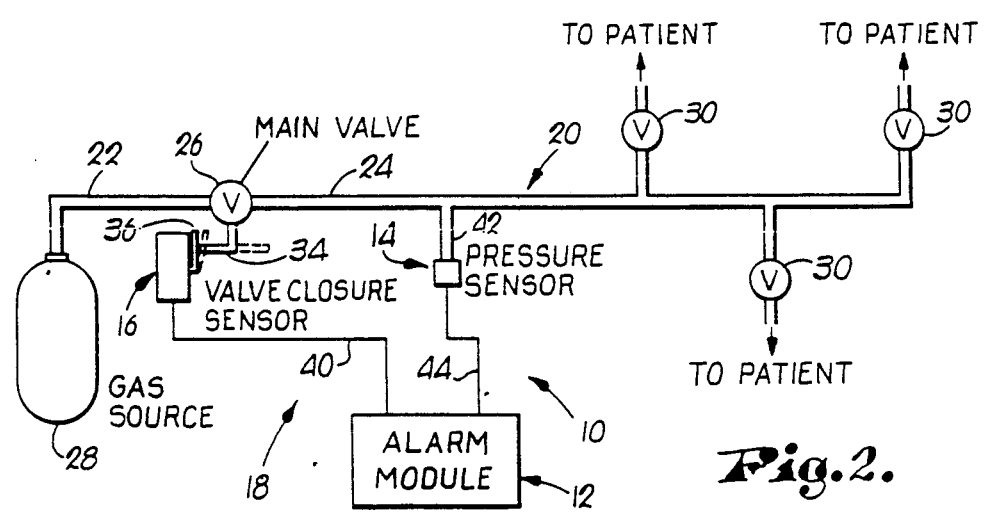

MEDICAL GAS ALARM SYSTEM

BACKGROUND OF THE INVENTION

1. Field of the Invention

This invention is broadly concerned with a medical gas alarm system which allows monitoring of a medical gas or vacuum delivery system for low or high pressure conditions or for system shutdown due to closure of a valve in the supply line. The alarm system provides a detection switch positioned for engagement with a valve closure device and a pressure sensor each coupled to an alarm module for transmitting an alarm signal when alarm conditions are detected.

2. Description of the Prior Art

Hospitals, nursing homes, clinics and a number of other health care institutions utilize medical gasses in rendering care to patients. It is well known to administer oxygen ($O_2$), air, nitrogen ($N_2$) and nitrous oxide ($NO_2$) to patients for treatment of a variety of different conditions or during surgical operations. In addition, medical gas systems also include evacuation systems which create a vacuum to be used in surgery or dentistry. A number of medical institutions now employ medical gas systems which use a central gas supply source for providing either a positive flow of treating gas or a negative flow of air to form a vacuum. These systems often utilize a network of conduits or supply lines to deliver the gas or supply the vacuum to treating locations remote from the central source. The networks often include main and branch shut-off valves to enable isolation of a portion of the network in the event of damage or fire, or to effect needed repairs.

Because the lives of patients may depend on receiving a reliable source of the treating gas, a real need has developed to ensure that the medical gas system is functioning properly, and to annunciate an alarm in the event a malfunction or alarm condition is detected. Such conditions may occur, for example, when the shut-off valve is either partially or fully closed. In that circumstance, the necessary supply of gas or the provision of vacuum may be insufficient. One example of an alarm system designed to detect valve closure is found in U.S. Pat. No. 4,879,547 to Pryslak, which shows the use of a fiber optic bundle looped though the lever of a valve and which detects closure of the valve when the fiber optic bundle is pulled out of a light detector.

There is a further need to detect other defects in the system which may impair the medical gas system effectiveness. For example, usage of the system may eventually result in low pressure conditions in the supply tank when the supply of gas is nearly exhausted. Alternatively, conditions such as a leak between the valve and the delivery outlet of the system may result in insufficient pressure or vacuum to sustain the necessary pressure level of the treating gas. There is a further need for early detection of these problems so that replacement sources of treating gas or vacuum may be provided to the patient before the medical gas delivery system becomes completely inoperative. Finally, due to the escalating costs associated with medical care and the shortage of trained nurses and technicians, monitoring of the medical gas delivery systems should be easy and capable of instant recognition of system faults at a single monitoring station remote from the supply line and valve.

SUMMARY OF THE INVENTION

These problems are largely solved by the medical gas alarm system of the present invention which monitors a medical gas system to detect alarm conditions including full or partial valve closure and high or low pressure conditions in the supply line on the delivery side of the valve. The system hereof broadly includes a sensor unit located on the delivery side of a valve of a medical gas supply system, a switch for determining the opened or closed status of the valve, and an alarm generator connected to the switch and the sensor for activating an alarm to warn of alarm conditions in the system such as high or low pressure or a closed or partially closed switch.

In the preferred embodiment of the medical gas alarm system hereof, the switch is a normally closed switch positioned for engaging a valve closure lever. When the lever is moved from a fully open position, an alarm signal is transmitted and an alarm is activated. The alarm generator is preferably an alarm module which may be interconnected to other modules or connected to an auxiliary output such as a mainframe computer. The sensor preferably serves to transmit a current to the alarm module which corresponds to the pressure in the system and thus the pressure may be displayed on the module. The sensor is located on the delivery side of the valve so that in the unlikely event the closure switch is deactivated or there is a loss of system pressure, the defect will be detected when pressure drops (or increases in the case of vacuum systems) below the desired level.

BRIEF DESCRIPTION OF THE DRAWINGS

FIG. 1 is a perspective view of the medical gas alarm system in accordance with the present invention showing a supply pipe and valve with a detection switch mounted on the valve and a sensor module pneumatically connected to the supply pipe, both the sensor module and detection switch being connected to the alarm module;

FIG. 2 is a schematic representation of a medical gas delivery system showing the pneumatic components and alarm module and the orientation of the alarm system thereon.

FIG. 4 is a schematic representation of a modular display incorporating several gas alarm systems as modular components thereof.

DESCRIPTION OF THE PREFERRED EMBODIMENT

Figure 3:
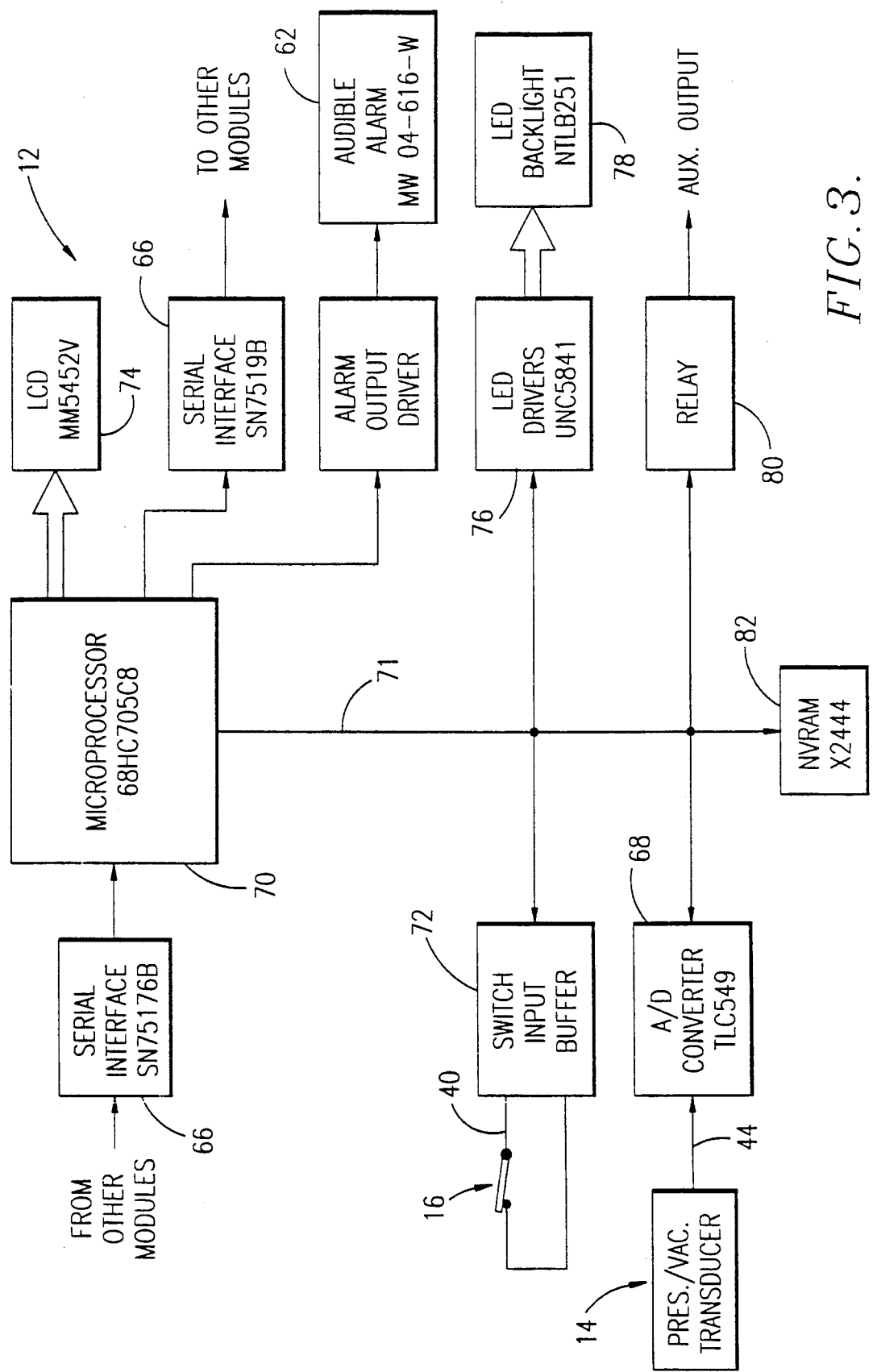
FIG. 3 is an electrical block diagram showing the operating components of the alarm system hereof.

Referring now to the drawings medical gas alarm system 10 in accordance with the present invention broadly includes an alarm module 12, sensor unit 14 and a detection switch 16. The medical alarm system 10 is configured for use with a medical gas delivery system 18 which typically includes a gas supply line 20 presenting a supply end 22 and a delivery end 24, and a shut-off valve 26 located intermediate the supply end 22 and the delivery end 24.

The medical gas delivery system 18 may provide either a gas under pressure or provide a source of vacuum whereby the supply end 22 draws a vacuum through the gas supply line 20. The gas under pressure may be oxygen ($O_2$), air, nitrogen ($N_2$), nitrous oxide ($NO_2$) or any other gas used in the medical field. As shown schematically in FIG. 2, the medical gas delivery system 18 conventionally includes a gas source 28 connected to supply line 20 and shut-off valve 26. The gas delivery system may include a number of zone valves as well as outlet valves 30 which are conventionally located at the point of delivery to the patient requiring treatment. In a vacuum system, gas source 28 represents an evacuation device which serves to maintain the desired vacuum in the system 10.

Returning to FIG. 1, the shut-off valve 26 includes a valve housing 32 and a control arm 34. Detection switch 16 is mounted on the valve housing 32 and includes a pivotally mounted foot 36. Foot 36 is positioned to engage control arm 34 when the valve 26 is in the fully open position, the foot 36 is pivoted whereby the normally closed contact within the switch body 38 is broken and the switch is in an open position. Switch 16 is operably connected to the alarm module 12 by a two-wire electrical cable 40.

Sensor unit 14 is preferably a temperature compensated pressure/vacuum transducer for sensing the pressure on the delivery end 24 of the valve 26 and transmitting a signal corresponding to that pressure to the alarm module 12. The transducer generates a signal from 4 to 20 milliamps and is conventionally available off the shelf from a variety of sources including Foxboro and IC Sensors. The sensor unit includes a gas service block which is connected to the delivery end 24 of the gas supply line 20 by an extension tube 42. As may be appreciated by those of ordinary skill in the art, the sensor unit 14 provides a polarized signal and thus is provided with a polarized connector whereby the signal generated by the sensor module 14 is properly transmitted along wiring 44 to alarm module 12.

As shown in FIG. 1, alarm module 12 presents a display panel 46 which includes a system status indicator 48, a digital readout 50 and a master valve indicator light 52. In addition, a gas identification label 54 is provided whereby the particular system being monitored may be readily identified. The system status indicator 48 includes a low pressure indicator 56, a high pressure indicator 58 and a normal status indicator 60. The low pressure indicator 56, high pressure indicator 58 and normal status indicator 60 are preferably individually and alternatively illuminated by light emitting diodes responsive to signals received from the sensor unit 14. Because the high pressure and low pressure indicators are visually perceptible warning displays, they are conventionally illuminated in red, whereas the normal status indicator 60 is illuminated in green.

The alarm module also includes an audible alarm 62 and is provided with an audible alarm silencing button 64. Silencing button 64 may be depressed to deactivate the audible alarm once the alarm module 12 receives an alarm condition signal.

FIG. 3 illustrates the operating components of module 12 in block diagram form using conventional components with standard industry part numbers shown where appropriate. Alarm module 12 is uniquely adapted to be connected to other similar modules through serial interfaces 66. Inputs to the alarm module 12 are received either from detection switch 16 or sensor unit 14, which as noted earlier is a commercially available 4 to 20 milliamp temperature compensated transducer. The signal corresponding to the pressure in the system 18 on the delivery end 24 of the valve 26 is transmitted through wiring 44 to an analog to digital (A/D) converter 68 and then to microprocessor 70. An alarm signal generated by opening of normally closed switch 16 is transmitted via electrical cable 40 to a conventional switch input buffer 72 and then to microprocessor 70 via a serial bus 71.

The microprocessor 70 processes the input from other modules through serial interface 66, switch input buffer 72 and from analog to digital converter 68 and transmits an output to the display panel 46 via serial bus 71. A signal corresponding to pressure in the supply line 20 as sensed by the sensor unit 14 is transmitted to a liquid crystal display (LED) 74 providing a digital readout 50. Output is also provided to a conventional alarm output driver for providing an alarm signal to audible alarm 62 whenever a high pressure, low pressure or other than open switch condition is detected by sensor unit 14 or detection switch 16. Microprocessor 70 also generates a signal to light emitting diode (LED) drivers 76 which activate respective light emitting diodes 78 corresponding to low pressure indicator 56, high pressure indicator 58 and normal status indicator 60. Output is also provided to a conventional electromechanical relay 80 to provide an isolated set of contacts which are activated in response to an alarm signal generated by the microprocessor for indicating to an auxiliary device, such as a mainframe computer, the existence of an alarm condition. Alternatively, the relay could be programmed to activate in response to any set of conditions wherein further data transmission and/or storage is desired. Finally, data is exchanged between the microprocessor 70 and a nonvolatile random access memory (NVRAM) 82 for comparing present system conditions against preselected alarm conditions.

It may be readily appreciated that different system conditions are appropriate and desirable according to the gas being employed. For example, the sensor unit 14 for use with oxygen, air or nitrous oxide would be adapted to monitor pressure in the range of 0–100 psi. For nitrogen, the range would preferably be 0–200 psi, while in a vacuum system, sensor unit would monitor vacuum in the range of 0–29 in. Hg. The alarm conditions may be preselected as desired, but it has been found that an alarm signal should ordinarily be generated when the pressure or the vacuum in the supply line increases or decreases 20% from normal. For example, the normal pressure in an oxygen system might preferably be 50 psi, and thus an alarm signal would be generated by the microprocessor 70 when the sensor unit 14 detects a pressure exceeding 60 psi or below 40 psi.

As may be well appreciated by those skilled in the art, the medical gas alarm system 10 in accordance with the present invention is coupled to a power supply 84 for providing a source of electrical current to the system components as shown in FIG. 4. Any conventional power supply unit capable of converting 120 V.A.C. to provide 12 and 24 volt current may be employed, but it has been found that the power supply module sold as Part No. 129178 from Puritan Bennett is especially suitable and enables a plurality of alarm systems 10 to be powered from a single power supply module. This power supply module also houses the audible alarm 62 that is provided with a ten wire panel buss cable 86 for transmitting power to the alarm module 12 and communicating the audible alarm signal to the audible alarm 62 housed in the power supply module.

Several sensor units 14, detection switch 16 and alarm modules 12 for various gas delivery systems 18 may be combined into a modular display 88 and powered by a single power supply unit module. The modular display 88 allows several gas alarm systems 10 to be interconnected for easy monitoring. It also eases adding or removing individual alarm modules as well as reducing overall cost.

In operation, the sensor unit 14 is connected to the alarm module by a polarized connector and mounted with the extension tube 42 in fluidic communication with the delivery end 24 of the supply line 20. The detection switch 16 is mounted on the shut-off valve 26 so that the control arm 34 engages the pivotally mounted foot 36 to open the normally closed detection switch 16. When power is supplied to the alarm system 10, the control arm 34 is depressing foot 36, and the supply line 20 is properly pressurized (or evacuated, as appropriate), the system is operating in a normal mode and no alarm signal is generated.

In the event the control arm 34 is displaced from its normal position wherein the valve 26 is other than fully open, an alarm condition exists when the arm 34 moves out of engagement with foot 36 and detection switch 16 closes. The closure of switch 16 creates an alarm signal which is relayed through switch input buffer 72 to microprocessor 70. The microprocessor in turn relays a signal to illuminate master valve 52 through an LED backlight 78 and the audible alarm 62 is activated and an auible alarm warning is generated thereby.

Similarly, in the event the pressure on the delivery end 24 of the valve 26 as detected by sensor unit 14 exceeds or falls below a preselected upper or lower limit stored in the non-volatile RAM, the microprocessor 70 initiates a signal to deactivate normal status indicator 60 and illuminate the LED backlight 78 corresponding to the low pressure indicator 56 or high pressure indicator 60, as appropriate. Again, the microprocessor 70 signals the audible alarm 62 to generate an audible alarm warning. The pressure level is also displayed by a liquid crystal display 74 providing digital readout 50.

In the event an alarm condition is detected either due to closure of the control arm 34 or pressure abnormality, the audible alarm 62 will be activated and an audible alarm signal generated. The user may readily identify the nature of the problem by noting whether or not the master valve light is illuminated or whether the system status reveals a pressurization malfunction. In the event the valve 26 is closed for, e.g. routine maintenance, the audible alarm may be deactivated by silencing button 64, but the closure of the valve 24 will still be indicated by illumination of master valve indicator 52 as a reminder that the valve must be reopened before normal operation may continue.

I claim:

1. A hospital medical gas delivery system for delivering gas to a plurality of physically separated delivery locations and for providing a perceptible alarm upon the occurrence of conditions leading to delivery system failure, said gas delivery system comprising:
   a main supply line adapted for coupling to a source of medical gas and including a main valve interposed therein, said main valve being shiftable through a range of positions between a first open position and a second, closed position;
   a distribution system downstream of and operatively coupled with said main valve, said distribution system including a plurality of distribution conduits respectively leading to said separated delivery locations, there being a distribution valve interposed in each of said distribution conduits;
   a sensor unit operatively connected with said distribution system downstream of said main valve and upstream of at least certain of said distribution valves, said sensor unit including structure for detecting pressure conditions within the distribution system, and for transmitting a first alarm condition signal when an improper pressure condition is sensed therein;
   switch means operatively coupled with said main valve for transmitting a second alarm condition signal when the valve is in other than said first position;
   alarm generating means for transmitting a humanly perceptible alarm warning; and
   signal processing means operatively coupling said sensor unit and switch means with said alarm generating means for receiving the respective first and second alarm condition signals from said switch means and sensor unit, and for actuating said alarm generating means upon sensing of improper pressure conditions within said distribution system or upon sensing of the position of said main valve in other than said first, open condition,
   whereby a humanly perceptible alarm is generated at a time after the onset of conditions leading to failure of the delivery system, but prior to actual failure thereof.

2. The delivery system as set forth in claim 1, said sensor unit comprising a temperature-compensated pressure/vacuum transducer.

3. The delivery system as set forth in claim 1, said main valve including a shiftable control arm, said switch means being located adjacent said control arm and including structure engagable by said control arm.

4. The delivery system as set forth in claim 1, said alarm generating means comprising structure for generating an audinle alarm.

5. The delivery system as set forth in claim 1, said alarm generating means including structure for generating separate, visually perceptible alarm displays responsive to respective alarm condition signals received from said sensor unit and said switch means.

6. The delivery system as set forth in claim 5, said visually perceptible alarm display corresponding to said sensor unit including both high pressure and low pressure alarm indicators.

7. The delivery system as set forth in claim 1, said alarm generating means including a relay adapted for indicating an alarm condition to a remotely located auxiliary device.

8. The delivery system as set forth in claim 1, said alarm generating means including means for connecting said alarm generating means in series to other similar alarm·generating means.

9. The delivery system as set forth in claim 1, said main supply line and distribution system being adapted for conveying a medical gas under positive pressure or vacuum.

* * * * *